(12) United States Patent
Nakamura et al.

(10) Patent No.: US 6,188,785 B1
(45) Date of Patent: Feb. 13, 2001

(54) PATTERN INSPECTING APPARATUS AND INSPECTING METHOD

(75) Inventors: Toyokazu Nakamura; Benjamin Tsai, both of Tokyo (JP)

(73) Assignee: NEC Corporation, Tokyo (JP)

( * ) Notice: Under 35 U.S.C. 154(b), the term of this patent shall be extended for 0 days.

(21) Appl. No.: 09/081,099

(22) Filed: May 19, 1998

(30) Foreign Application Priority Data

May 20, 1997 (JP) .................................................. 9-129673

(51) Int. Cl.[7] .................................................. G06K 9/00
(52) U.S. Cl. .......................... 382/149; 382/147; 348/126
(58) Field of Search .................................. 382/144, 145, 382/147, 149, 151; 356/394; 348/87, 126

(56) References Cited

U.S. PATENT DOCUMENTS

| | | | |
|---|---|---|---|
| 4,262,280 | * 4/1981 | Kochert ................................. | 382/254 |
| 4,579,455 | * 4/1986 | Levy et al. ............................ | 356/394 |
| 5,576,833 | * 11/1996 | Miyoshi et al. ...................... | 356/394 |

FOREIGN PATENT DOCUMENTS

| | | |
|---|---|---|
| 61-82107 | 4/1986 | (JP) . |
| 61-200415 | 9/1986 | (JP) . |

OTHER PUBLICATIONS

K. Levy et al., "4579455: Photomask Inspection Apparatus and Method with Improved Defect Detection", Patent Server: 4579455 Detailed View, 1997, pp. 1–3.

* cited by examiner

*Primary Examiner*—Bhavesh Mehta
(74) *Attorney, Agent, or Firm*—Sughrue, Mion, Zinn, Macpeak & Seas, PLLC

(57) ABSTRACT

An image signal of a large number of patterns of the same shape on an LSI wafer obtained by an image sensor is held in a memory circuit, by using a CMOS image sensor chip incorporating a one-dimensional CMOS photodiode array, an analog-to-digital conversion circuit, a memory circuit and a processing circuit. Then, the image signal and one-cycle and two-cycle displaced image signals cyclically displaced from the image signal by the processing circuit are algebraically processed by a defect detection algorithm in the processing circuit of the CMOS image sensor. By this processing, a defect image is extracted without using a normal inspection pattern. Thus, a high-speed processing, a simplification of a configuration of an apparatus and a miniaturization of the apparatus become possible.

6 Claims, 4 Drawing Sheets

PATTERN INSPECTING APPARATUS AND INSPECTING METHOD

BACKGROUND OF THE INVENTION

1. Field of the Invention

The present invention relates to a pattern inspecting apparatus and a pattern inspecting method for inspecting a minute or fine pattern of a semiconductor memory such as a DRAM having memory cells formed in an array shape on a wafer and a mask to be used for manufacturing the wafer.

2. Prior Art

There has been disclosed a conventional minute or a fine pattern inspecting apparatus in, for example, Japanese Patent Application Laid-open No. 61-200415. FIG. 1 is a block diagram for showing the conventional minute pattern inspecting apparatus similar to the apparatus disclosed in the publication. In FIG. 1, a reference numeral 410 denotes an image processing and a system control unit, 412 an image memory, 413 an image processing auxiliary unit, 414 an auxiliary image memory, 415 an image display circuit, 416 a display, 417 a stage control circuit, 421 a light source, 423 a CCD image sensor, 441 an XY stage, 445 a specimen to be inspected, 451 an irradiation beam, 452 a reflected beam, and 453 an image signal.

In this example, a general optical beam is used instead of an electron beam source for the light source. Referring to FIG. 1, this apparatus includes the image processing and system control unit 410, the light source 421 as a beam irradiating unit for generating an image, the CCD image sensor 423 as a detector, the image memory 412 for storing the image signal 453 by having an input of this image signal, the image processing auxiliary unit 413, the auxiliary image memory 414 for storing a normal inspection pattern, the image display circuit 415, the display 416 for displaying a result of an inspection, the XY stage 441 for moving the specimen to be inspected 445, and the stage control circuit 417 for controlling the XY stage.

An inspection of a minute pattern by this apparatus is performed in the following manner. The irradiation beam 451 is irradiated onto the specimen to be inspected 445 on the XY stage 441 from the light source 421 for generating an image. The reflected beam 452 having image information such as a surface shape or the like of the specimen to be inspected 445 is detected by the CCD image sensor 423. The image signal 453 obtained from the CCD image sensor 423 is stored in the image memory 412. The image processing and system control unit 410 extracts a defect on the specimen to be inspected 445 by comparing image information obtained through the image processing auxiliary unit 413 and normal inspection pattern data prepared separately and called from the auxiliary image memory 414.

The image processing and system control unit 410 further calculates a position of a defect based on the above information and information of a stage position obtained from the stage control circuit 417, and displays on the display 416 a position of the defect on the specimen to be inspected 445 through the image display circuit 415.

The conventional minute or fine pattern inspecting apparatus shown in FIG. 1 has the following problems.

At First, at the time of comparing the inspection data pattern with the pattern obtained from the specimen to be inspected, it is necessary to match an image position for recognizing the pattern, taking a relatively long time for the calculation. Further, for carrying out a pattern recognition in high accuracy, it is necessary to move the stage in high accuracy. As a result, the apparatus tends to be larger in size, making it relatively difficult to perform a rapid move of the stage. Moreover, as the comparison operation is carried out in one image frame unit, a large amount of memories are required, leading to a large-size apparatus.

SUMMARY OF THE INVENTION

It is an object of the present invention to provide a pattern inspecting apparatus and an inspecting method therefor capable of increasing a processing speed, simplifying a configuration of the apparatus and miniaturizing the apparatus.

A pattern inspecting apparatus according to the present invention is an apparatus for performing an appearance inspection of a minute defect in a large number of repeated patterns of the same shape within individual chips formed on an LSI wafer. This apparatus includes a moving stage for loading a specimen to be inspected, which can be moved for positioning said specimen to be inspected, a stage control unit for driving the moving stage and outputting positional information, a light source for irradiating an irradiation beam to be projected to the specimen to be inspected, a microscopic optical system for collecting reflected beams by irradiating an irradiation beam to the specimen to be inspected, a CMOS image sensor chip incorporating a one-dimensional photodiode array for receiving a reflected beam, an analog-to-digital conversion circuit for converting a received image signal into a digital signal, a memory circuit for storing a converted image signal, and a processing circuit for processing an image signal for detecting a defect, a display unit for displaying a result of an inspection, and a system control unit for controlling each unit.

A method for inspecting a pattern according to the present invention is a method for performing an appearance inspection of a minute or fine defect in a large number of repeated patterns of the same shape within individual chips formed on an LSI wafer. This method includes the steps of moving a specimen to be inspected to a predetermined position, projecting an irradiation beam to minute pattern elements with repeated same patterns formed on the specimen to be inspected, receiving a reflected beam by light receiving elements laid out in one dimension and converting the received beam into an analog signal string, converting the analog signal string obtained into a digital signal string and storing it as an original digital signal string, cyclically displacing the stored original digital signal string into one-cycle and two-cycle displaced signal strings of repeated cycles of patterns respectively and storing them, algebraically processing the stored one-cycle displaced digital signal string and two-cycle displaced digital signal string and the stored original digital string to extract a defect image, and generating and displaying defect information of the specimen to be inspected from the defect image obtained and positional information of the minute pattern elements inspected.

According to the present invention, in an apparatus for performing an appearance inspection of a minute defect in a large number of repeated patterns of the same shape within individual chips formed on an LSI wafer, the use of a CMOS image sensor chip incorporating a one-dimensional CMOS photodiode array, an analog-to-digital conversion circuit, a memory circuit and a processing circuit makes it possible to provide a compact minute pattern inspecting apparatus which avoids the need for matching a normal inspection pattern with an image, shortens the calculation time and requires no large amount of memories.

According to the present invention, it is possible to extract a defect image without using a normal inspection pattern by the method including the steps of holding in a memory circuit an image signal of a large number of patterns of the same shape on an LSI wafer obtained by an image sensor, cyclically displacing this image signal into one-cycle and two-cycle displaced signals of repeated patterns respectively by using a processing circuit, and by carrying out an algebraic processing to the original image signal and the cyclically displaced signals by a defect detection algorithm.

The minute pattern inspecting apparatus and the method of the present invention have a characteristic in that a defect image is extracted by obtaining an image with the use of a CMOS image sensor chip, holding in a memory circuit an image signal of minute patterns consisting of minute pattern elements formed repeatedly on a specimen inspected within the chip, cyclically displacing this image signal into one-cycle and two-cycle displaced image signals of repeated patterns by using a processing circuit, and by algebraically processing this image signal between the one-cycle and two-cycle displaced images signals. Since an image obtained by displacing a one-dimensional image itself is used as a reference image by using an image processing circuit within the chip connected in parallel direct to the image sensor at an extremely short distance, the number of processing steps for a defect extraction can be reduced with an improved processing speed as compared with an apparatus and a method used conventionally. Further, as a one-dimensional image of an own image is sequentially used at each time of scanning, a large number of memories are not necessary, ensuring a simplification and miniaturization of the structure of the apparatus.

Effects of the present invention are summarized as follows. A first effect is that the time required for extracting a defect image can be reduced. This is because an image matching processing by a pattern recognition required in the prior-art technique is not necessary at the time of comparing inspection pattern data with a pattern obtained from a specimen to be inspected. A second effect is that a stage moving speed can be made faster, with a resultant high-speed inspection of a specimen as a whole. Further, an apparatus itself can be made compact. This effect is obtained as the conventionally-required image positioning by a pattern recognition is not necessary. A third effect is that the structure of an apparatus is made simple. This is because the conventionally-required comparison processing and a large volume of memories required for this processing are not necessary.

DESCRIPTION OF THE PREFERRED EMBODIMENT

Figure 1:
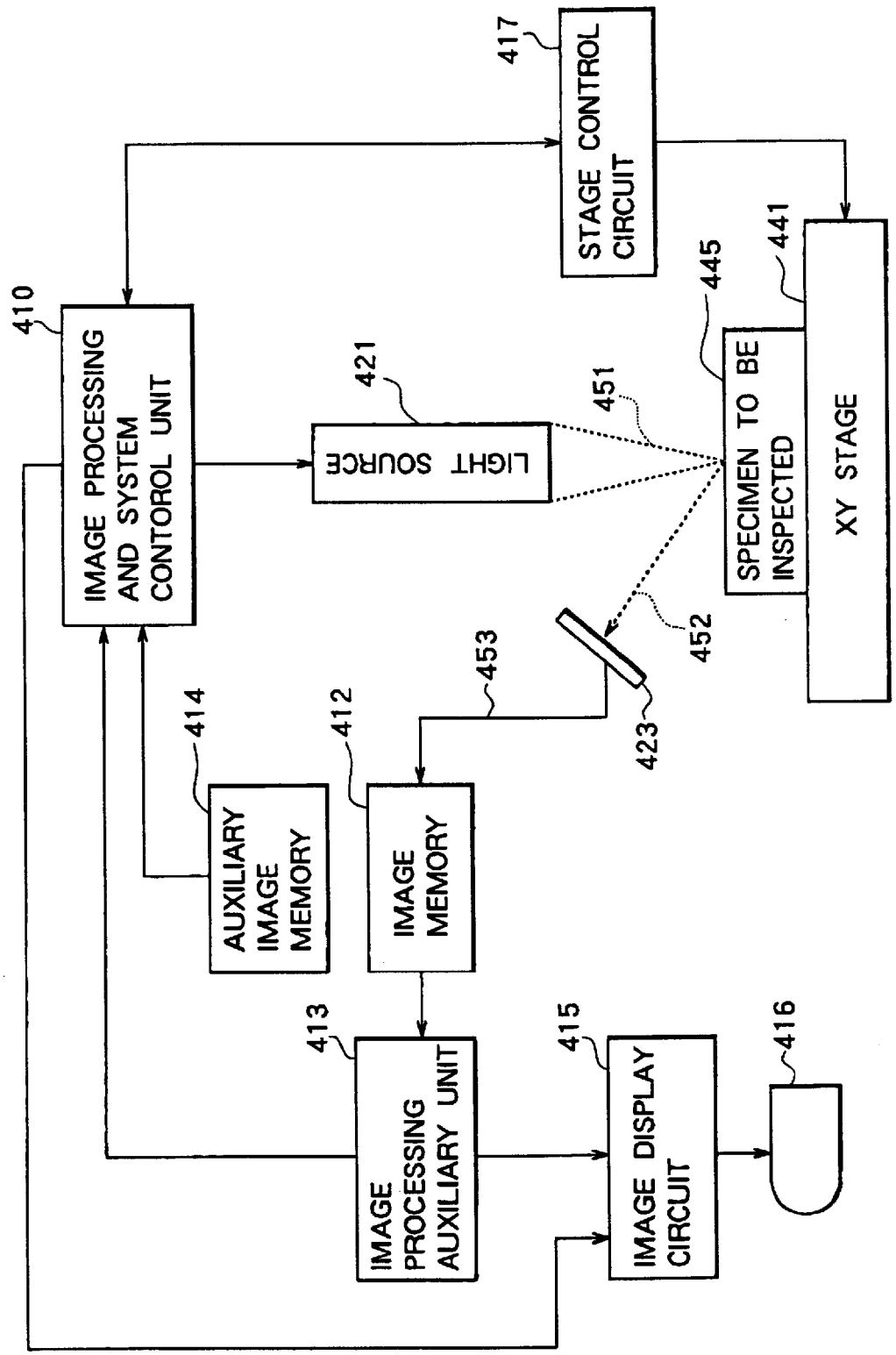
FIG. 1 is a block diagram for showing a conventional minute or fine pattern inspecting apparatus.
Figure 2:
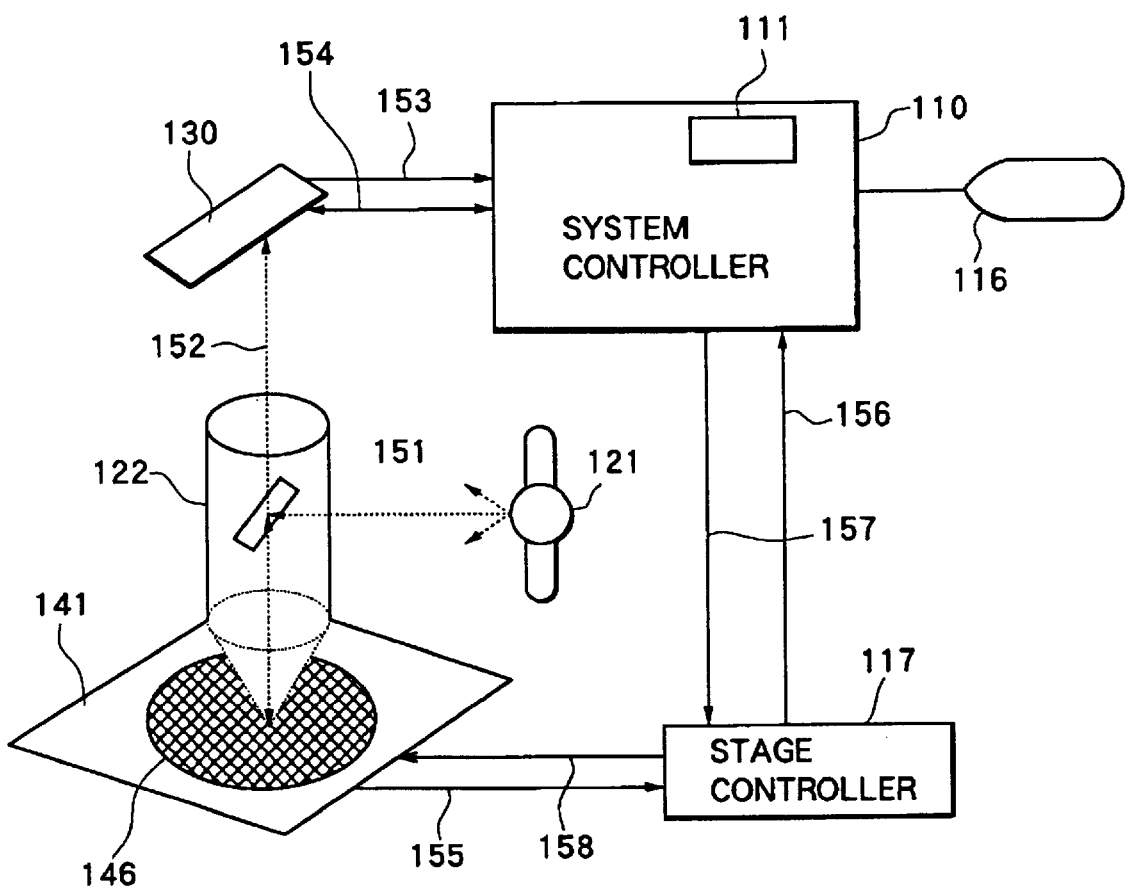
FIG. 2 is a block diagram for showing a configuration of a minute or fine pattern inspecting apparatus relating to an embodiment of the present invention.

A mode of implementation of the present invention will be explained below with reference to the drawings. FIG. 2 is a block diagram of a minute pattern inspecting apparatus relating to an embodiment of the present invention. In FIG. 2, a reference numeral 110 denotes a system controller, 111 a recording medium, 116 a display, 117 a stage controller, 121 a light source, 122 a microscopic optical system, 130 a CMOS image sensor chip, 141 an XY stage, 146 a specimen to be inspected, 151 an irradiation beam, 152 a reflected beam, 153 defect image information, 154 a defect detection control signal/image sensor operation status information, 155 and 156 XY stage positional information, 157 an XY stage drive control signal, and 158 an XY stage drive signal.

Figure 3:
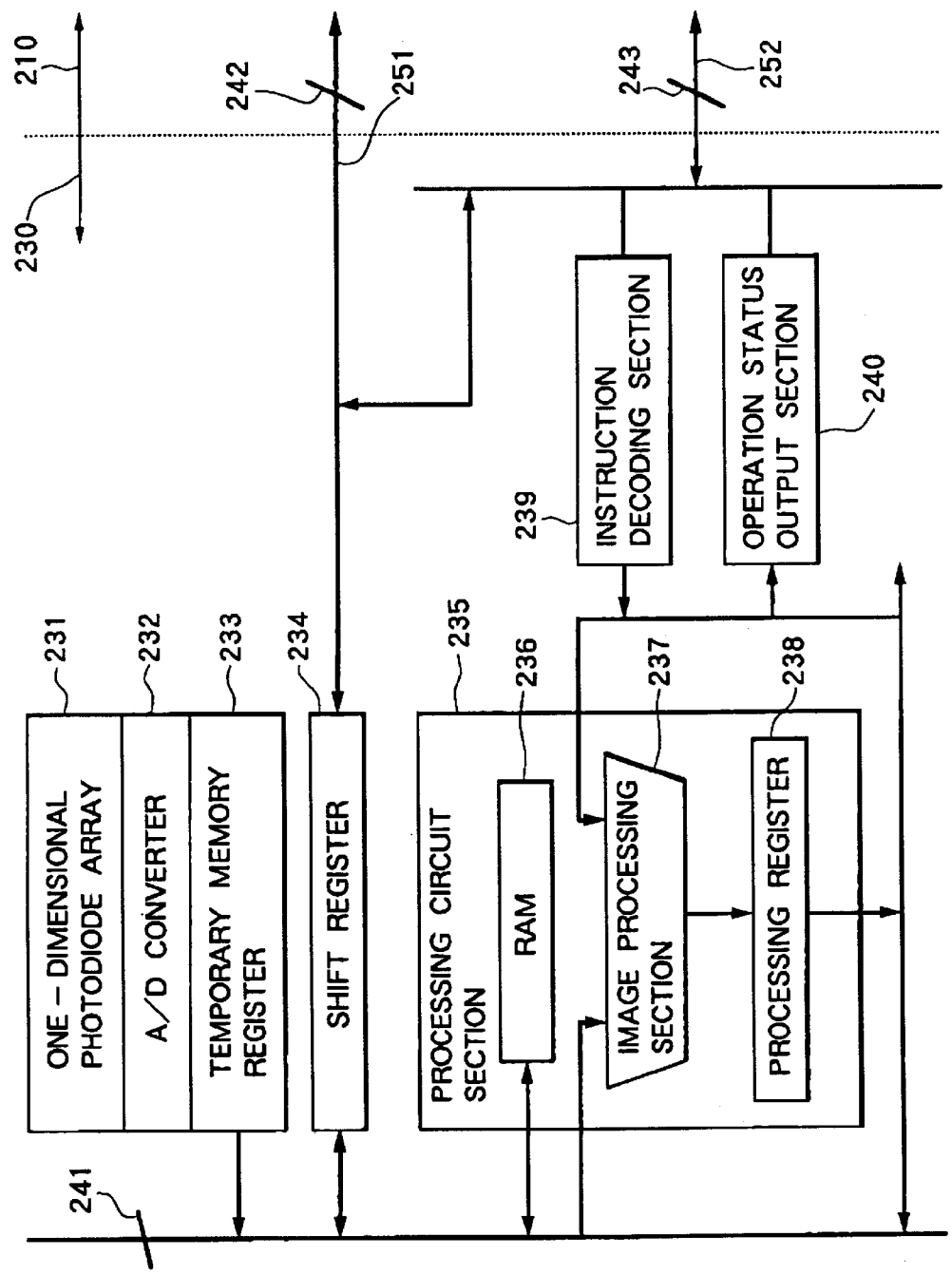
FIG. 3 is a block diagram for showing a signal processing block and a flow of signals within a CMOS image sensor chip in the embodiment of the present invention.

FIG. 3 is a block configuration diagram for showing a signal processing section and a flow of signals within the CMOS image sensor chip 130 shown in FIG. 2. In FIG. 3, a reference numeral 210 denotes a system controller side, 230 a CMOS image sensor chip side, 231 a one-dimensional photodiode array, 232 an A/D converter, 233 a temporary memory register, 234 a shift register, 235 a processing circuit section, 236 a RAM, 237 an image processing section, 238 a processing register, 239 an instruction decoding section, 240 an operation status output section, 241 a 256-bit bus, 242 an 8-bit bus, 243 a 16-bit bus, 251 a reference image input/defect image output signal, and 252 a control instruction input/operation status output signal.

Figure 4:
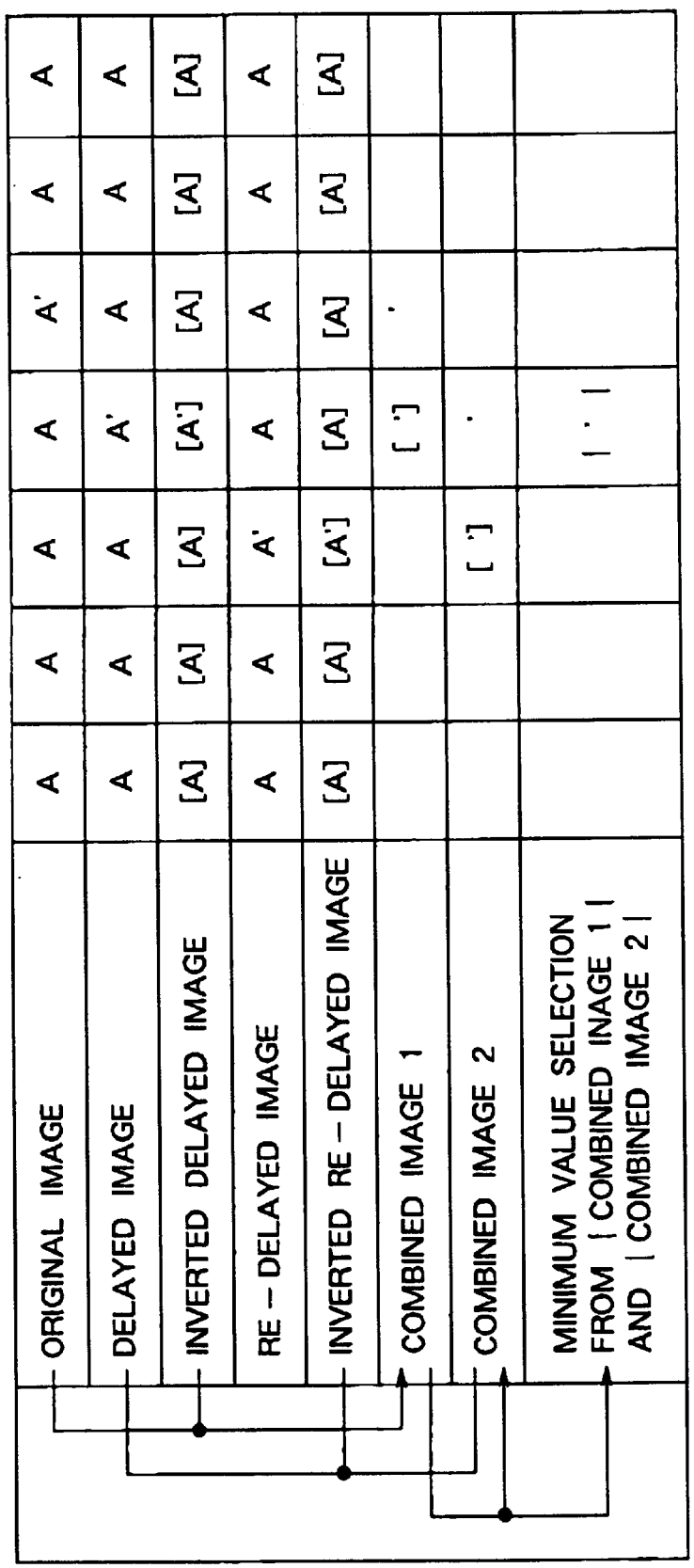
FIG. 4 is a diagram for explaining a defect extraction algorithm performed within the CMOS image sensor chip in the embodiment of the present invention.

FIG. 4 is a diagram for explaining a conception of defect extraction algorithm performed within the CMOS image sensor chip in the embodiment of the present invention. A minute pattern on a specimen being tested has basically a plurality of pattern elements "A" formed in an array shape. In FIG. 4, a normal pattern element is expressed as "A", a defect as "'", a pattern element having a defect as "A'", and an inverted image as ["A"]. A minute pattern on the specimen to be inspected also includes a defect pattern element "A'" in addition to normal pattern elements "A".

In the present apparatus, as shown in FIG. 2, a beam is irradiated from the light source 121 onto a minute pattern consisting of minute pattern elements (such as memory cells) formed repeatedly on the specimen to be inspected 146 such as a wafer of a semiconductor memory like a DRAM or the like having memory cells formed in an array shape. Then, through the microscopic optical system 122, an appearance image of the minute pattern elements is taken into the CMOS image sensor chip 130 by the one-dimensional photodiode array 231 shown in FIG. 3. Thereafter, analog luminance signal strings stored in all the photodiode cells in the one-dimensional photodiode are A/D converted simultaneously in parallel by the parallel A/D converters 232 of the same number as that of the photodiode cells incorporated in the CMOS image sensor chip 130, and digital signal strings obtained substitute the information in the temporary memory register 233.

Next, bits of the digitized one-dimensional image information are stored simultaneously in parallel as digital signal strings in the RAM 236 of the processing circuit section 235 provided similarly in the CMOS image sensor chip 130 through the transfer buses 241 of the same number as that of the bits of the temporary register. The one-dimensional image information as the digital signal strings also substitutes the information in the processing register 238 provided separately in the processing circuit section 235. A one-cycle cyclically displaced image of the repeated patterns in the one-dimensional image is formed as a digital signal string by the image processing section 237, and this digital signal string is stored in a space area in the RAM 236. Further, a two-cycle cyclically displaced image of the repeated patterns in the one-dimensional image is formed as a digital signal string by the image processing section 237 and the processing register 238, and this digital signal string is stored in a remaining space area in the RAM 236.

In this manner, the one-dimensional image information of pattern elements, the image information cyclically displaced by one cycle of the repeated pattern and the image information cyclically displaced by two cycles of the repeated pattern are stored as digital signal strings in the RAM 236.

Using these three image information, defect information is extracted by the CMOS image sensor chip 130 through the application of a defect detection algorithm to be described later, and the defect information is output to the system controller 110 as the defect image information 153. The defect image information 153 and the positional information of the specimen 146 obtained from the stage controller 117 form defect information in the system controller 110, and this defect information can be transmitted to the outside through the display 116.

The algorithm will be explained next with reference to FIG. 4.

The image detecting unit of the present apparatus either detects at once an image of a predetermined area of minute patterns on a specimen to be inspected or detects an image of a predetermined area by scanning. A displaced image (displaced digital signal string) having the pattern elements "A" and "A'" cyclically displaced by the cycle of the repeated pattern elements from an original image (original digital signal string) can be displayed by moving the displaced image to right or left by the displaced amount with respect to the original digital signal string of the image signal of minute patterns of a predetermined area obtained by the image detection. This is a phenomenon similar to a ghost phenomenon of a broadcast TV image received with a superimposition of an image reflected by a building or the like. Because of the similarity of this phenomenon, a displaced image will hereinafter be called a delayed image.

When a displaced amount (delayed amount) in this case is adjusted by repeated cycles of a pattern element (an integer times a pattern element), an original image of a certain pattern element can be superimposed on the delayed image of a different pattern element, for example, an adjacent pattern element. Further, when the delayed image is changed to be a delayed inverted image by inverting the luminance of the delayed image and the original image and the delayed inverted image are combined by an algebraic operation, the pattern elements "A" of mutually the same shape are offset as image information (combined image 1). In this case, if the defect pattern element "A'" exists in the minute pattern, the above offset effect does not work on this defect portion both in a combined image of the original image "A'" relating to the defect pattern element "A'" and the delayed inverted image "[A]" and in a combined image of the delayed inverted image "[A']" and the original image "A". As a result, the combined images become a defect image "'" and an inverted defect image "[']" respectively. Further, a re-delayed image having the delayed image further displaced by the same amount and a re-delayed inverted image having this re-delayed image inverted are formed. By combining the re-delayed inverted image and the delayed image, a combined image 2 can be formed which is similar to the combined image 1 except the pattern elements are shifted by one pattern. Next, absolute values of the combined image 1 and the combined image 2 are obtained, then the absolute values of the respective pattern elements are compared, and a minimum value selection processing for selecting an image with a smaller value including zero is carried out. By this processing, the defect image in the combined image 1 and the combined image 2 respectively positioned at left or right side of the defect position in the delayed image has a value of zero as the combined image 2 and the combined image 1 with which the combined image 1 and the combined image 2 are compared respectively do not include this defect image. The combined image 1 and the combined image 2 at the defect position of the delayed image both have this defect image, and therefore, this defect image remains in the combined images 1 and 2. Thus, an absolute-valued defect image |'| corresponding to the defect of the image shifted by one pattern element from the defect position of the original image can be obtained.

According to the present apparatus, a defect image can be detected by using an algorithm for detecting a defect by the above-described processing. Thus, an inspector can confirm an existence of a defective pattern element by detecting a defect image.

It is easily analogized that the above-described steps can also be achieved by a software such as a program recorded in the recording medium 111.

While in the above mode of implementation, the present invention has been explained for a wafer of a semiconductor memory, the present invention can also be applied similarly to an inspection of a minute pattern in a mask or the like used for a manufacturing of a semiconductor memory of a similar structure.

For example, a detection of a minute defect was carried out on an 8-inch wafer having a layout of 90 16-MB DRAM chips, by using a one-dimensional CMOS image sensor chip which is a product of IVP, a Swedish manufacturer, as a CMOS image sensor, and by combining this with a commercially available general image intensifier for increasing a light quantity for a microscopic optical system. As a result, it was possible to carry out the detection three times faster as compared with the case where an apparatus with a conventional CCD image sensor was used.

What is claimed is:

1. A pattern inspecting apparatus for performing a surface inspection of an LSI wafer which contains a plurality of individual chips thereon, in order to identify fine or minute defects in a surface pattern of said chips, wherein the same surface pattern is repeated on each of said chips, said pattern inspecting apparatus comprising:

a moving stage for supporting a specimen to be inspected thereon, said moving stage being movable for positioning said specimen;

a stage control unit for driving said moving stage and for outputting positional information;

a light source for providing an irradiation beam over a predetermined area for projection onto said specimen to be inspected;

a microscopic optical system for projecting the irradiation beam onto said specimen and for directing a reflected irradiation beam onto a sensor;

a CMOS image sensor chip comprising:

a one-dimensional photodiode array for receiving the reflected beam from said microscopic optical system and for producing an analog image signal, wherein a one dimensional image of the predetermined area on the specimen is detected at once and a two-dimensional image of the predetermined area on the specimen is obtained by moving said moving stage to enable inspection of an entire surface of the specimen;

an analog-to-digital conversion circuit for converting the analog image signal into a digital image signal;

a memory circuit for storing the digital image signal;
an image processing section for cyclically displacing the digital image signal;
a processing circuit for processing the image signal to detect a defect therefrom; and
display means for displaying a result of the inspection.

2. A minute pattern inspecting method for performing a surface inspection of an LSI wafer which contains a plurality of individual chips thereon, in order to discover a defect in a surface pattern of said chips, wherein the same surface pattern is repeated on each of said chips, comprising the steps of:

(a) moving a specimen for inspection to a predetermined position defined by position information;

(b) projecting an irradiation beam over a predetermined area of said LSI wafer;

(c) receiving, on light receiving elements laid out in one dimension, a beam reflected from said LSI wafer, wherein a one dimensional image of the predetermined area on the LSI wafer is detected at once and a two-dimensional image of the predetermined area of the LSI wafer is obtained by moving said moving stage to enable inspection of the entire surface of the LSI wafer;

(d) converting the received beam into an analog signal string;

(e) converting the analog signal string into a digital signal string;

(f) storing the digital signal string as an original digital signal string;

(g) cyclically displacing the repeated patterns stored as an original digital signal string by a first cycle and a second cycle, respectively, to obtain first and second displaced signal strings corresponding to the original digital signal string;

(h) storing the first and second displaced signal strings;

(i) inverting the first and second displaced signal strings;

(j) storing the inverted first and second displaced signal strings;

(k) algebraically processing the stored first cycle displaced digital signal string, the stored second cycle displaced digital signal string, the stored inverted first and second displaced signal strings, and the stored original digital string to extract a defect image; and (l) generating and displaying defect information of said inspected specimen from the defect image obtained in step (k) and positional information of step (a).

3. A minute pattern inspecting method for performing an appearance inspection of a defect in a large number of repeated patterns of the same shape within individual chips formed on an LSI wafer, comprising the steps of:

moving a specimen to be inspected to a predetermined position;

projecting an irradiation beam over a predetermined area to minute pattern elements with repeated same patterns formed on the specimen to be inspected;

receiving a reflected beam by light receiving elements laid out in one dimension and converting the received beam into an analog signal string, wherein a one dimensional image of the predetermined area on the specimen is detected at once and a two-dimensional image of the predetermined area of the specimen is obtained by moving said moving stage to enable inspection of the entire surface of the specimen;

converting the analog signal string obtained into a digital signal string and storing it as an original digital signal string;

cyclically displacing the stored original digital signal string to obtain one-cycle and two-cycle displaced signal strings of repeated cycles of patterns respectively, which correspond to the original digital signal string, and storing the displaced signal strings;

algebraically processing the stored one-cycle displaced digital signal string and two-cycle displaced digital signal string and the stored original digital string to extract a defect image;

generating and displaying defect information of the specimen to be inspected from the defect image obtained and positional information of the minute pattern elements inspected, wherein said algebraic processing step for extracting a defect image comprises the steps of:

generating a first combined image by combining the original digital signal string and an inverted digital signal string having the original digital signal string displaced by one cycle;

generating a second combined image by combining the one-cycle displaced digital string and an inverted digital signal string having a the original digital signal string displaced by two cycles cycle;

comparing respective absolute values of the first combined image and the second combined image at the same position and selecting a smaller absolute value including zero; and extracting, as a defect image, a corresponding minute pattern element of the one-cycle displaced digital signal string at a position having an absolute value other than zero.

4. A recording medium having recorded a control program for performing a surface inspection of an LSI wafer which contains a plurality of individual chips thereon, in order to discover a minute defect in a surface pattern of said chips, wherein the same surface pattern is repeated on each of said chips, said recording medium being readable by a machine to execute the procedures of:

(a) moving a moving stage having loaded thereon a specimen to be inspected through a stage control unit, and positioning said specimen at a predetermined position defined by position information;

(b) projecting an irradiation beam irradiated from a light source over a predetermined area onto said LSI wafer;

(c) receiving, on light receiving elements laid out in one dimension, a reflected beam from said LSI wafer, wherein a one dimensional image of the predetermined area on the specimen is detected at once and a two-dimensional image of the predetermined area of the specimen is obtained by moving said moving stage to enable inspection of the entire surface of the specimen;

(d) converting the received reflected beam into an analog signal string;

(e) converting the analog signal string into a digital signal string by an analog-to-digital converting circuit;

(f) storing the converted signal in a memory circuit as an original digital signal string;

(g) cyclically displacing, in a processing circuit, the repeated patterns stored as an original digital signal string into a first cycle and a second cycle, respectively, to obtain first and second displaced signal strings which correspond to the original digital signal string;

(h) storing the first and second displaced signal strings in a memory circuit;

(i) inverting the first and second displaced signal strings;

(j) storing the inverted first and second displaced signal strings;

(k) algebraically processing the stored first cycle displaced digital signal string, the stored second cycle displaced digital signal string, the stored inverted first and second displaced signal strings, and the stored original digital signal string by said processing circuit to extract a defect image; and (l) generating defect information of said inspected specimen by a system controller from the defect information obtained by said processing circuit in step (k) and positional information of the inspected minute pattern elements from the stage control unit of step (a), and displaying the defect information using display means.

5. A pattern inspecting apparatus for performing a surface inspection of an LSI wafer which contains a plurality of individual chips thereon, in order to discover fine or minute defects in a surface pattern of said chips, wherein the same surface pattern is repeated on each of said chips, said pattern inspecting apparatus comprising:

a moving stage which supports a specimen to be inspected thereon and is movable for positioning said specimen;

a stage control unit in communication with said moving stage to position said moving stage, said stage control unit also outputs positional information to a system controller;

a light source which provides an irradiation beam over a predetermined area;

a microscopic optical system which projects the irradiation beam onto said specimen and directs a reflected irradiation beam onto a sensor; and a CMOS image sensor chip comprising:

a one-dimensional photodiode array which receives the reflected beam from said microscopic optical system and produces an image signal, wherein a one dimensional image of the predetermined area on the specimen is detected at once and a two-dimensional image of the predetermined area of the specimen is obtained by moving said moving stage to enable inspection of the entire surface of the specimen;

an analog-to-digital conversion circuit, which receives the image signal from said one-dimensional photodiode array and converts the image signal into a digital image signal;

a memory circuit which receives and stores the digital image signal;

an image processing section which cyclically displaces the digital image signal;

a processing circuit which receives and processes the digital image signal to detect a defect therefrom; and a display which receives the defect information from the processing unit and displaying a result of the inspection.

6. A minute pattern inspecting method according to claim 2, wherein said algebraic processing of step (k) comprises the steps of:

generating a first combined image by combining the original digital signal string and an inverted digital signal string having the original digital signal string displaced by said first cycle;

generating a second combined image by combining said first cycle displaced digital string and an inverted digital signal string having a the original digital signal string displaced by said second cycle;

comparing respective absolute values of the first combined image and the second combined image at the same position and selecting a smaller absolute value including zero; and extracting, as a defect image, a corresponding minute pattern element shifted a first cycle from a position having an absolute value other than zero.

* * * * *